(12) United States Patent
Berry et al.

(10) Patent No.: US 7,943,792 B2
(45) Date of Patent: May 17, 2011

(54) PRODUCTION OF BIODIESEL, CELLULOSIC SUGARS, AND PEPTIDES FROM THE SIMULTANEOUS ESTERIFICATION AND ALCOHOLYSIS/HYDROLYSIS OF MATERIALS WITH OIL-CONTAINING SUBSTITUENTS INCLUDING PHOSPHOLIPIDS AND PEPTIDIC CONTENT

(75) Inventors: William W. Berry, Lakeland, FL (US); Mark G. Tegen, Gig Harbor, WA (US); William Rusty Sutterlin, Hoover, AL (US)

(73) Assignee: Inventure Chemical Inc., Tuscaloosa, AL (US)

( * ) Notice: Subject to any disclaimer, the term of this patent is extended or adjusted under 35 U.S.C. 154(b) by 124 days.

(21) Appl. No.: 12/243,933

(22) Filed: Oct. 1, 2008

(65) Prior Publication Data

US 2009/0198077 A1 Aug. 6, 2009

Related U.S. Application Data

(63) Continuation-in-part of application No. 12/061,038, filed on Apr. 2, 2008.

(60) Provisional application No. 60/921,327, filed on Apr. 2, 2007.

(51) Int. Cl.
C07C 51/43 (2006.01)
(52) U.S. Cl. ...................................... 554/174

(58) Field of Classification Search ................. None
See application file for complete search history.

(56) References Cited

U.S. PATENT DOCUMENTS 2,237,624 A 4/1941 Oldham
(Continued)

FOREIGN PATENT DOCUMENTS

CN 1122568 5/1996
(Continued)

OTHER PUBLICATIONS

Kreutzer, Manufactureo fatty alcohols based on natrual fats and oils, 1984, JAOCS, vol. 61, No. 2. pp. 343-348.*

(Continued)

*Primary Examiner* — Jafar Parsa
*Assistant Examiner* — Yate K Cutliff
(74) *Attorney, Agent, or Firm* — Frommer Lawrence & Haug LLP; Shelly M. Fujikawa

(57) ABSTRACT

The present invention relates to a method for producing fatty acid alkyl esters as well as cellulosic simplified sugars, shortened protein polymers, amino acids, or combination thereof resulting from the simultaneous esterification and hydrolysis, alcoholysis, or both of algae and other oil containing materials containing phospholipids, free fatty acids (FFA), glycerides, or combination thereof as well as polysaccharides, cellulose, hemicellulose, lignocellulose, protein polymers, or combination thereof in the presence of an alcohol and an optional acid catalyst.

12 Claims, 2 Drawing Sheets

U.S. PATENT DOCUMENTS

| | | |
|---|---|---|
| 2,383,601 A | 8/1945 | Keim |
| 2,434,110 A | 1/1948 | Hatch et al. |
| 2,494,366 A | 1/1950 | Sprules et al. |
| 3,068,303 A | 12/1962 | Pattison |
| 3,098,882 A | 7/1963 | Arnold |
| 3,109,804 A | 11/1963 | Martin |
| 3,205,281 A | 9/1965 | Fleming et al. |
| 3,260,759 A | 7/1966 | Skinner |
| 3,296,325 A | 1/1967 | Gross et al. |
| 3,376,960 A | 4/1968 | Bender |
| 3,486,588 A | 12/1969 | Grego |
| 3,552,533 A | 1/1971 | Nitz |
| 3,916,031 A | 10/1975 | Beal |
| 4,068,747 A | 1/1978 | Snoy |
| 4,164,506 A | 8/1979 | Kawahara et al. |
| 4,173,269 A | 11/1979 | Craig |
| 4,280,962 A | 7/1981 | Watanabe et al. |
| 4,561,233 A | 12/1985 | Harter et al. |
| 4,665,158 A | 5/1987 | Armanet et al. |
| 4,695,411 A | 9/1987 | Stern et al. |
| 4,698,186 A | 10/1987 | Jeromin et al. |
| 4,852,645 A | 8/1989 | Coulon et al. |
| 4,874,893 A | 10/1989 | Flork |
| 4,885,668 A | 12/1989 | Maglica et al. |
| 4,912,260 A | 3/1990 | Dobson et al. |
| 4,930,606 A | 6/1990 | Sporzynski et al. |
| 5,012,860 A | 5/1991 | Mukherjee |
| 5,015,789 A | 5/1991 | Arntz et al. |
| 5,023,043 A | 6/1991 | Kotzlowski et al. |
| 5,093,537 A | 3/1992 | Unruh et al. |
| 5,174,368 A | 12/1992 | Boury et al. |
| 5,180,597 A | 1/1993 | Hamm |
| 5,182,075 A | 1/1993 | Gotoh et al. |
| 5,210,318 A | 5/1993 | Briggs et al. |
| RE34,349 E | 8/1993 | Unruh et al. |
| 5,256,827 A | 10/1993 | Slaugh et al. |
| 5,298,637 A | 3/1994 | Cooper |
| 5,334,778 A | 8/1994 | Haas et al. |
| 5,343,660 A | 9/1994 | Caoduro et al. |
| 5,358,633 A | 10/1994 | Dai et al. |
| 5,364,984 A | 11/1994 | Arntz et al. |
| 5,382,715 A | 1/1995 | Vargas et al. |
| 5,389,595 A | 2/1995 | Simpson et al. |
| 5,390,217 A | 2/1995 | Ioki et al. |
| 5,399,793 A | 3/1995 | Vargas et al. |
| 5,449,653 A | 9/1995 | Briggs et al. |
| 5,454,454 A | 10/1995 | Easton et al. |
| 5,455,370 A | 10/1995 | Demmering et al. |
| 5,456,666 A | 10/1995 | Campbell et al. |
| 5,475,134 A | 12/1995 | Baker |
| 5,525,126 A | 6/1996 | Basu et al. |
| 5,596,085 A | 1/1997 | Silver et al. |
| 5,773,657 A | 6/1998 | Rutter et al. |
| 5,778,033 A | 7/1998 | Filipuzzi et al. |
| 5,786,524 A | 7/1998 | Powell et al. |
| 5,814,112 A | 9/1998 | Elliott et al. |
| 5,817,594 A | 10/1998 | McNamara et al. |
| 5,888,380 A | 3/1999 | Fujita et al. |
| 5,910,241 A | 6/1999 | McNamara et al. |
| 5,916,838 A | 6/1999 | Wulff-Doring et al. |
| 5,936,126 A | 8/1999 | Ruhl et al. |
| 5,945,570 A | 8/1999 | Arhancet et al. |
| 5,958,825 A | 9/1999 | Wulff-Doring et al. |
| 5,972,118 A | 10/1999 | Hester et al. |
| 5,977,013 A | 11/1999 | Elliott et al. |
| 6,093,845 A | 7/2000 | van Acker et al. |
| 6,152,975 A | 11/2000 | Elliott et al. |
| 6,232,511 B1 | 5/2001 | Haas et al. |
| 6,342,464 B1 | 1/2002 | Arhancet et al. |
| 6,376,720 B1 | 4/2002 | Han |
| 6,399,538 B1 | 6/2002 | Hucul |
| 6,399,800 B1 | 6/2002 | Haas et al. |
| 6,423,857 B1 | 7/2002 | Copeland et al. |
| 6,429,167 B1 | 8/2002 | Maeno et al. |
| 6,432,469 B1 | 8/2002 | Remmereit et al. |
| 6,660,506 B2 | 12/2003 | Nguyen et al. |
| 6,670,300 B2 | 12/2003 | Werpy et al. |
| 6,762,496 B2 | 7/2004 | Yamamoto et al. |
| 6,768,015 B1 | 7/2004 | Luxem et al. |
| 6,855,838 B2 | 2/2005 | Haas et al. |
| 6,911,566 B2 | 6/2005 | Tsunoda et al. |
| 6,933,398 B2 | 8/2005 | Peter et al. |
| 6,961,190 B1 | 11/2005 | Tamaoki et al. |
| 6,965,044 B1 | 11/2005 | Hammond et al. |
| 7,449,313 B2 | 11/2008 | Rush |
| 2002/0077492 A1 | 6/2002 | Goto et al. |
| 2002/0087036 A1 | 7/2002 | Haas et al. |
| 2003/0158074 A1 | 8/2003 | Haas et al. |
| 2003/0229237 A1 | 12/2003 | Haas et al. |
| 2004/0059143 A1 | 3/2004 | Peter et al. |
| 2004/0097764 A1 | 5/2004 | Tsunoda et al. |
| 2004/0103934 A1 | 6/2004 | Szumlic et al. |
| 2004/0182749 A1 | 9/2004 | Domokos et al. |
| 2004/0225161 A1 | 11/2004 | Sunkara et al. |
| 2004/0260125 A1 | 12/2004 | Seapan et al. |
| 2005/0020842 A1 | 1/2005 | Haas et al. |
| 2005/0033099 A1 | 2/2005 | Ryu et al. |
| 2005/0080300 A1 | 4/2005 | Komplin et al. |
| 2005/0112735 A1 | 5/2005 | Zappi et al. |
| 2005/0274065 A1 | 12/2005 | Portnoff et al. |
| 2006/0155138 A1 | 7/2006 | Haas et al. |
| 2007/0100162 A1 | 5/2007 | Petrus et al. |
| 2007/0232817 A1 | 10/2007 | Pereira et al. |
| 2008/0051593 A1 | 2/2008 | Berry et al. |
| 2008/0160593 A1 | 7/2008 | Oyler |
| 2009/0071064 A1 | 3/2009 | Machacek et al. |

FOREIGN PATENT DOCUMENTS

| | | |
|---|---|---|
| CN | 1342521 | 4/2002 |
| CN | 1342633 | 4/2002 |
| CN | 1428190 | 7/2003 |
| CN | 1428322 | 7/2003 |
| CN | 1699516 | 11/2005 |
| FR | 2191939 | 2/1974 |
| GB | 829475 | 3/1960 |
| GB | 966270 | 8/1964 |
| GB | 1011270 | 11/1965 |
| GB | 1436458 | 5/1976 |
| GB | 2015509 | 9/1979 |
| GB | 1581379 | 12/1980 |
| GB | 2073232 | 10/1981 |
| JP | 54084508 | 7/1979 |
| JP | 2004182622 | 7/2004 |
| WO | WO-9745390 | 12/1997 |
| WO | WO-0000456 | 1/2000 |
| WO | WO-02/074881 | 9/2002 |
| WO | WO-03/085070 A2 | 10/2003 |
| WO | WO-2004/103934 A2 | 12/2004 |
| WO | WO-2005/058856 A1 | 6/2005 |
| WO | WO-2006116193 | 11/2006 |
| WO | WO-2008086495 | 7/2008 |
| WO | WO-2008122029 | 10/2008 |

OTHER PUBLICATIONS

Sasaki et al., dissolution and hydrolysis of cellulose in subcritical and supercritical water, 2000, Ind. ENg. Chem. Res. 39, pp. 2883-2890.*

Sato et al., Reaction Kinetics of Amino Acid decompositoin in high-temperature and high-pressure water, 2004, Ind. Eng. Chem. Res. 43, pp. 3217-3222.*

Warabi et al., Biodiesel fuel from vegetable oil by various supertical alcohols, 2004, Applied Biochemistry and Biotechnology, vp;/ 113-116, pp. 793-801.*

Lewis, Richard J. Sr. editor., "Hawley's Condensed Chemical Dictionary," Van Nostrand Company, New York), 12th edition, 1993, title page, bibliography page, pp. 34, 507.

Aldrich Handbook of Fine Chemicals and Laboratory Equipment, 2000-2001, title page, pp. 1012, 1252, 1266, 1521.

Notice of Publication of U.S. Appl. No. 10/337,604, filed Jan. 7, 2003.

Hui, Y. H., "Bailey's Industrial Oil and Fat Products," Edible Oil and Fat Products: Processing Technology, (John Wiley Sons, Inc. New York), 5th Edition, 1996, 4:56-57.

Swern, D., "Bailey's Industrial Oil and Fat Products," 4th Edition, vol. 2, 1982, pp. 290-292.

Graboski, M.S. et al., "Combustion of Fat and Vegetable Oil Derived Fuels in Diesel Engines," Prog. Energy Combust. Sci., 1998, 24:125-164.

Krawczyk, T., "Biodiesel," Inform, Aug. 1996, 7(8):801, 804-808, 810.

Haas, M. J. et al., "Engine Performance of Biodiesel Fuel Prepared from Soybean Soapstock: A High Quality Renewable Fuel Produced from a Waste Feedstock", Energy & Fuels, 2001, 15(5):1207-1212.

Foglia, Thomas A. et al., "Quantitation of Neutral Lipid Mixtures Using High Performance Liquid Chromatography with Light Scattering Detection," J. Liq. Chrom. & Rel. Technol., 1997, 20(12):1829-1838.

Standard Specification for Biodiesel Fuel (B100) Blend Stock for Distillate Fuels, Designation D 6751-02, American Society for Testing and Materials, West Conshohocken, Pa, 2002.

Peterson, C.L. et al., "Processing, Characterization, and Performance of Eight Fuels from Lipids," Applied Engineering in Agriculture, 1997, 13(1):71-79.

Freedman, B. et al., "Variables Affecting the Yields of Fatty Esters from Transesterified Vegetables Oils," J. Am. Oil Chem. Soc., Oct. 1984, 61(10):1638-1643.

Mittlebach, Martin et al. "Diesel Fuel Derived from Vegetable Oils, III. Emission Tests Using Methyl Esters of Used Frying Oil," J. Am. Oil Chem. Soc., Jul. 1998 65(7):1185-1187.

Haas, M. J. et al., "Enzymatic Approaches to the Production of Biodiesel Fuels," Lipid Biotechnology, (Marcel Dekker, Inc. New York) 2002, pp. 587-598.

Canakci, M. et al., "Biodiesel Production from Oils and Fats with High Free Fatty Acids," American Society of Agricultural Engineers, 44(6):1429-1436 (2001).

Singer, Brian et al., "The Simultaneous Analysis of Proteins, Lipids, and Diterpenoid Resins Found in Cultural Objects," Annali di Chimica (Rome, Italy), 2007, 97(7):405-417.

Boldizsar, I. et al., "Simultaneous GC-MS Quantitation of Acids and Sugars in the Hydrolyzates of Immunostimulant, Water-Soluble Polysaccharides of Basidiomycetes," Chromatographia, Apr. 1998, 47(7/8):413-419.

Harrington, Kevin J. et al., "Transesterification in Situ of Sunflower Seed Oil," Ind. Eng. Chem. Prod. Dev., 1985, 24:314-318.

Kildiran, Gokhan et al., "In-Situ Alcoholysis of Soybean Oil," JAOCS, 1996, 73(2):225-228.

International Search Report and Written Opinion, mailing date Jul. 7, 2008, for International Patent Application Serial No. PCT/US08/59096 filed Apr. 2, 2008.

Huber, G. W. et al., "Synthesis of Transportation Fuels from Biomass: Chemistry, Catalysts, and Engineering," American Chemical Society, 106(9):4044-4098, Sep. 2006.

Ben-Amotz, Ami et al. "Chemical Profile of Selected Species of Microalgae with Emphasis on Lipids," J.Phycol. 21, 72-81 (1985).

Hudson, Bertram et al. "The Lipids of the Alga *Spirulina*," J.Sci.Fd Agric. 1974, 25, 759-763.

Suen, Yu et al. "Total Lipid Production of the Green Alga *Nannochloropsis* Sp. QII Under Different Nitrogen Regimes," J.Phycol. 23, 289-296 (1987).

Sheehan, John et al. "A Look Back at the U.S. Department of Energy's Aquatic Species Program—Biodiesel from Algae," National Renewable Energy Laboratory, Jul. 1998 (328 pages).

Demirbas, A., "Biodiesel production via non-catalytic SCF method and biodiesel fuel characteristics," Energy Conversion & Management, vol. 47, pp. 2271-2282, 2006.

Yin, J., et al., "Self-oganization of oligopeptides obtained on dissolution of feather keratins in superheated water,"Biomacromolecules, vol. 8, pp. 800-806, Jan. 26, 2007.

Sanders et al. "Bio-Refinery as the Bio-Inspired Process to Bulk Chemicals," Feb. 13, 2007, Macromol Biosci, vol. 7, pp. 105-117 (13 pages).

* cited by examiner

PRODUCTION OF BIODIESEL, CELLULOSIC SUGARS, AND PEPTIDES FROM THE SIMULTANEOUS ESTERIFICATION AND ALCOHOLYSIS/HYDROLYSIS OF MATERIALS WITH OIL-CONTAINING SUBSTITUENTS INCLUDING PHOSPHOLIPIDS AND PEPTIDIC CONTENT

CROSS REFERENCE TO RELATED APPLICATIONS

The present patent application is a continuation-in-part of U.S. application Ser. No. 12/061,038 filed Apr. 2, 2008 which claims the benefit of U.S. provisional patent application Ser. No. 60/921,327 filed on Apr. 2, 2007. The contents of these prior applications are hereby incorporated by reference and in their entireties.

FIELD OF THE INVENTION

The present invention pertains to the esterification of phospholipids, free fatty acids (FFAs) and glycerides with alcohol optionally in the presence of an acid catalyst to form fatty acid alkyl esters. The present invention further pertains to the simultaneous esterification and hydrolysis/alcoholysis of a feedstock containing phospholipids, free fatty acids (FFAs), glycerides, or a combination thereof as well as cellulosic material, proteins, or both in the presence of an alcohol and, optionally, acid catalyst to form fatty acid alkyl esters as well as cleaved cellulosic material, shorter peptides, amino acids, or a combination thereof.

BACKGROUND OF THE INVENTION

Over the past three decades interest in the reduction of air pollution, and in the development of domestic energy sources, has triggered research in many countries on the development of non-petroleum fuels for internal combustion engines. For compression ignition (diesel) engines, it has been shown that the simple alcohol esters of fatty acids (biodiesel) are acceptable alternative diesel fuels. Biodiesel has a higher oxygen content than petroleum diesel, and therefore reduces emissions of particulate matter, hydrocarbons, and carbon monoxide, while also reducing sulfur emissions due to a low sulfur content.

For spark ignition (gasoline) engines, ethanol, produced by fermentation of simple sugars generated from corn starch, can be blended with petroleum gasoline to substitute petroleum content with renewable content fuel, reduce dependence on foreign oil, reduce carbon dioxide emissions, and improve octane in the blended fuel. Since both ethanol and biodiesel are made from agricultural materials, which are produced via photosynthetic carbon fixation (e.g., by plants and by animals that consume plants), the combustion of biodiesel and ethanol does not contribute to net atmospheric carbon levels.

Initial efforts at the production, testing, and use of biodiesel employed refined edible vegetable oils (e.g. soybean oil, canola oil), used cooking oils (e.g. spent fryer oils) and animal fats (e.g., beef tallow) as feedstocks for fuel synthesis (Krawczyk, T., INFORM, 7: 800-815 (1996); Peterson, C. L., et al., Applied Engineering in Agriculture, 13; 71-79 (1997); Holmberg, W. C., and J. E. Peeples, Biodiesel: A Technology, Performance, and Regulatory Overview, National Soy Diesel Development Board, Jefferson City, Mo. (1994)). Simple alkali-catalyzed transesterification technology (Freedman, B., et al., J. Am. Oil Chem. Soc., 61(10): 1638-1643 (1984)) is efficient at esterifying the acylglycerol-linked fatty acids of such feedstocks and is employed in making these fuels. More recently, methods have been developed to produce fatty acid methyl esters (FAME) from cheaper, less highly refined lipid feedstocks such as spent restaurant grease (Mittelbach, M., and P. Tritthart, J. Am. Oil Chem. Soc., 65(7):1185-1187 (1988); Graboski, M. S., et al., The Effect of Biodiesel Composition on Engine Emissions from a DDC Series 60 Diesel Engine, Final Report to USDOE/National Renewable Energy Laboratory, Contract No. ACG-8-17106-02 (2000); Haas, M. J., et al., Enzymatic Approaches to the Production of Biodiesel Fuels, in Kuo, T. M. and Gardner, H. W. (Eds.), Lipid Biotechnology, Marcel Dekker, Inc., New York, (2002), pp. 587-598).

In addition to acylglycerols, less highly refined lipid feedstocks can contain substantial levels of free fatty acids (FFA) and other nonglyceride materials. Biodiesel synthesis from these feedstocks can be accomplished by conventional alkaline catalysis, which then requires an excess of alkali since the FFA (which are not esterified by this method) are converted to their alkali salts. These alkali salts can cause difficulties during product washing due to their ready action as emulsifiers. Ultimately, the alkali salts are removed and discarded. This approach thus involves a loss of potential product, increases catalyst expenses, and can entail a disposal cost.

Further, with higher FFA levels, i.e. typically in excess of 2%, a general approach is to utilize an acid esterification step, since at higher FFA values the extent of soap formation with a single stage, transesterification process is excessive and renders the process uneconomical and potentially unworkable. To handle the higher FFA content, a two step process involving first acid-catalyzed esterification of the free fatty acids and then alkali-catalyzed transesterification of glyceride-linked fatty acids can be employed to achieve conversion of mixed, heterogeneous feedstocks (Canakci, M., and J. Van Gerpen, Biodiesel Production from Oils and Fats with High Free Fatty Acids, Abstracts of the 92.sup.nd American Oil Chemists' Society Annual Meeting & Expo, p. S74 (2001); U.S. Pat. Nos. 2,383,601; 2,494,366; 4,695,411; 4,698,186; 4,164,506). However, these methods can require multiple acid-catalyzed esterification steps to reduce the concentration of free fatty acids to acceptably low levels. In addition, high separation efficiency is required between the two stages to minimize the potential for acid catalyst transfer into the base catalyst section.

The feedstocks used for current biodiesel production are conventional commodity materials, thus they have other established markets which basically set the minimum commodity prices. As a result, the bulk of the biodiesel production cost relates to the feedstock cost. While there are a number of established process technologies in the biodiesel industry, as a result of the feedstock cost being such a high factor (i.e. 75% to 80%) there is a surprisingly small difference between the various processes in overall operational costs (due to this feedstock factor).

The production of ethanol for fuel use is well established and the growth in this industry over the past 2 decades has been significant. Fermentation is an (obviously) old process going back literally thousands of years to early wine and beer making. The basic techniques remain the same, however in the modern ethanol production process highly efficient enzymes and yeasts have been developed to provide for more efficient conversion of the fermentable materials. Further, the process technology associated with fuel grade ethanol production has also advanced over the years, e.g. energy recovery, so that current technology has a high degree of efficiency.

The primary feedstocks for current commercial ethanol production are corn (primarily in the United States) and sugar (especially in Brazil). As in the biodiesel case, these materials are "conventional" agricultural commodities and have historically had various markets associated with them, i.e. food sources and the like. It is also apparent that since these are commodity products, there are various non-fuel market pressures that dictate price. As such, for ethanol production, as in the case of biodiesel, the feedstock represents the vast majority of the operating cost (i.e. as much as 80%).

For both the biodiesel and ethanol fuel markets and for the large-scale expansion of the renewable fuels industries, it is apparent that development of a potentially large scale, lower cost feedstock source would be advantageous. Recently, significant advances have been made in carbon dioxide sequestering technology (aquatic species program reference, NREL, GFT, a U.S. company) using various species of algae to provide photosynthetic carbon fixation. This technology has tremendous value when applied to industrial sources of carbon dioxide such as; coal fired power generation, natural gas fired power generation, petroleum fired power generation, industrial gas generation, cement manufacturing, industrial fermentation, as well as various additional industries that are significant emitters of carbon dioxide. The algae resulting from the photosynthetic carbon fixation represents an opportunity for the production of transportation fuels as well as various value added chemical products. The volume of algae produced per acre, in a designed pond or "farming" system, is estimated at between 200,000 pounds to 600,000 pounds per year of algae on a dry basis; and is substantially greater, in terms of oil content and fermentable material content, than the volume of soybeans or corn produced per acre at 2,500 pounds to 10,000 lbs per year. The volume of algae produced using the above method allows for a far greater production density versus corn or soybeans with a relatively small geographic footprint. In addition, the algae selected comprise free fatty acids (FFA), triglycerides, polysaccharides, cellulose, hemicellulose and/or lignocellulose. However, the economical processing of the selected algae provides significant challenges for conventional biofuel processing techniques.

For the algae scenario, a significant degree of pretreatment of the sludge is required to prepare the material for the more traditional solvent extraction methods to recover the contained oil. This front-end pretreatment would then need to be combined with multi-stage esterification, (for free fatty acid esterification) and transesterification (for triglyceride conversion), and a completely separate process would be required for acid hydrolysis of the lipid depleted algae pulp to produce monosaccharides, disaccharides, trisaccharides or polysaccharides for production of ethanol by fermentation. This series of processing steps would add significant cost to the resulting materials to be produced from algae. Therefore, there is a need for further development of simplified processing routes for the production of fatty acid alkyl esters (i.e. FAME), monosaccharides, disaccharides, trisaccharides or polysaccharides in a simplified, direct process.

In addition, the current growth in biofuel production from food commodities is generating a substantial increase in co-products such as corn distillers grains, sorghum distillers grains, and rice bran meal. These co-products have underutilized value from the cellulosic content (45-55% by mass) and oil content (7-22% by mass) which represent an opportunity to increase the supply of biofuels to market by simply increasing the processing efficiency of current methods.

Again, the interest in cellulosic feeds for ethanol has increased considerably over the past several years, however some of the same issues apply to this source as to feeds such as algae. For example, with cellulosic feeds the typical approaches include enzyme treatment followed by yeasts which convert the cellulosic materials to sugars and subsequent alcohol, but has little effect on any contained oil content. For example distillers grains have both cellulosic content as well as contained oil values, both of which could be useful for conversion to biofuels.

Thus, there remains a significant need in the art to develop a simple and efficient method for the production of biofuels and ethanol from renewable energy sources.

SUMMARY OF THE INVENTION

The present invention relates to a method for making fatty acid alkyl esters by (a) combining a feedstock with an alcohol and, optionally, an acid catalyst and (b) reacting the combination at a pH in the range of 0 to 7, at a temperature in the range of 140° C. to 300° C., wherein the feedstock comprises (a) phospholipids, free fatty acids (FFAs), glycerides, or a combination thereof and (b) cellulosic material, proteins, or both and wherein the reaction products comprise (a) fatty acid alkyl esters and (b) cleaved cellulosic material, shortened proteins, amino acids, or a combination thereof. The pressure of this reaction can be in a range of 500 psig to 2800 psig or sufficient to prevent boiling of the alcohol during the reaction.

The following reactions can occur in the above method: (a) the transesterification or esterification of phospholipids into fatty acid alkyl esters, (b) the direct esterification of FFAs into fatty acid alkyl esters, (c) the transesterification of glycerides into fatty acid alkyl esters, (d) the hydrolysis, alcoholysis, or both of the cellulosic material into cleaved cellulosic material, and (e) the hydrolysis, alcoholysis, or both of protein into shorter peptides, amino acids, or both.

The present invention is further directed to the product from the reaction of the feedstock with the alcohol and, optionally, acid catalyst.

DETAILED DESCRIPTION OF THE INVENTION

The present invention relates to a method for producing fatty acid alkyl esters as well as cellulosic simple sugars, shortened protein peptide polymers, and amino acids involving esterifying and performing hydrolysis, alcoholysis, or both on a material containing phospholipids, free fatty acids, glycerides, or a combination thereof as well as polysaccharides, cellulose, hemicellulose, lignocellulose, protein, or combination thereof with an alcohol and an optional acid catalyst.

Figure 1:
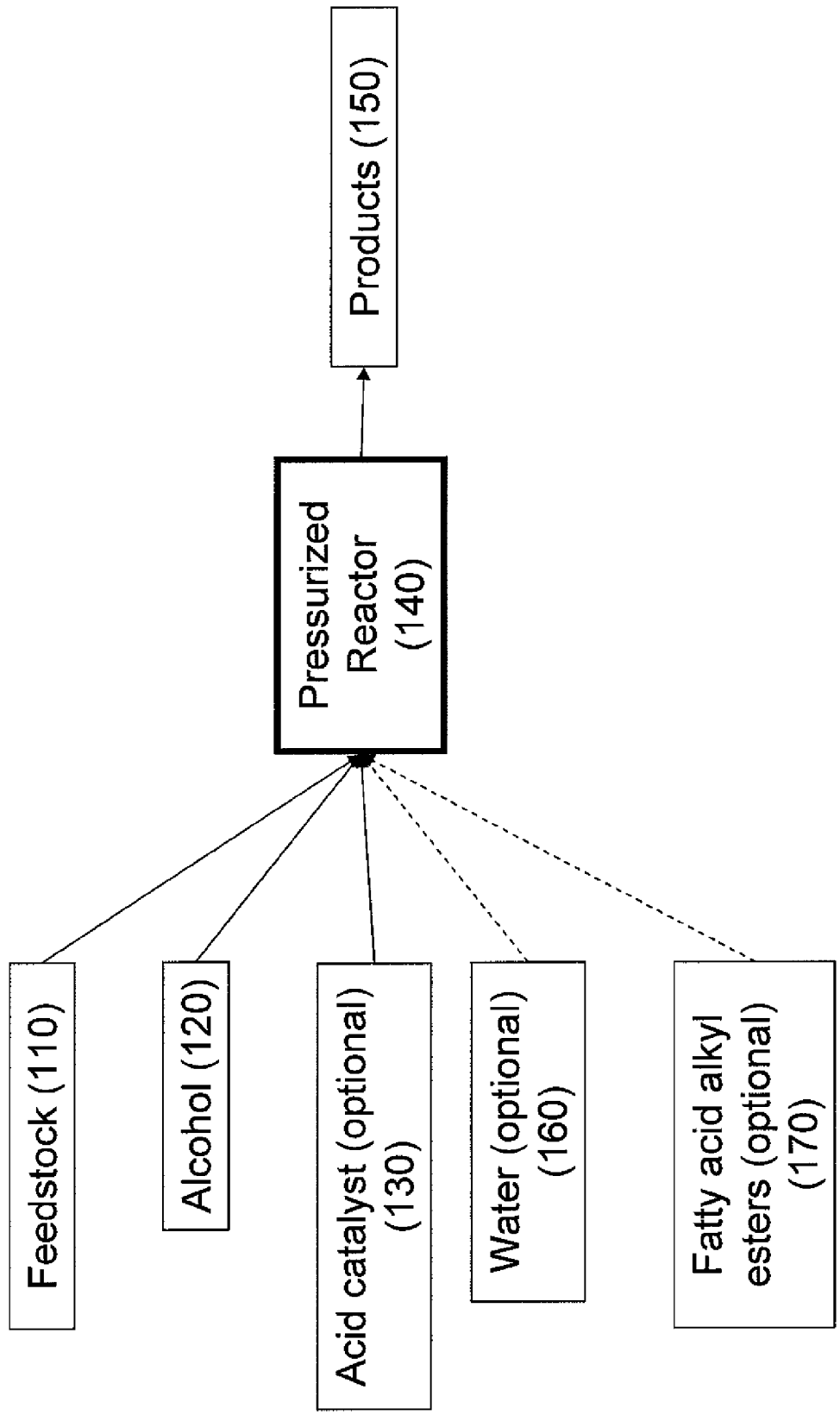
FIG. 1 provides a schematic of the reaction of the feedstock (110) with the alcohol (120) in the presence of the optional acid catalyst (130) and optionally in the presence of water (160) and fatty acid alkyl esters (170) in a pressurized reactor (140) to products (150).

Prior to the present invention, the conversion of biomass into biofuel and ethanol was a time-consuming and multi-step procedure that was both economically inefficient and wasteful. Additionally, conventional methods are inhibited by the presence of water. In contrast, a fast, single-step, and efficient method for the conversion of biomass into biofuel and sugars to produce ethanol can be performed in the presence of water. FIG. 1 illustrates a method of the present invention in which feedstock (110) is reacted with alcohol (120) in the presence of an optional acid catalyst (130) and optionally in the presence of water (160) and fatty acid alkyl esters (170) in a pressurized reactor to yield products (150).

The feedstock for this process can be, for example, algae (e.g., fresh or salt water algae, prokaryotic algae), dried distillers grains (DDG) from, e.g., corn or sorghum, rice bran, jatropha seed, palm seed, vegetable oil seeds (e.g., soybean, canola), eukaryota, protozoa, phytoplankton, cyanobacteria, bacteria, corn ethanol fermentation residuals, or other oil-containing material that may also contain potentially fermentable cellulosic material (e.g., polysaccharides, cellulose, hemicellulose, and lignocellulose), protein, or both. The oils of the feed stock can include phospholipids, FFAs, monoglycerides, diglycerides, triglycerides, or a combination thereof. The feedstock can also be a combination of different oil-containing materials.

The feedstock can contain from about 0 wt % to about 100 wt % phospholipids, e.g., from about 5 wt % to about 50 wt % phospholipids. The feedstock can contain from about 0 wt % to about 100 wt % FFA, e.g., from about 5 wt % to about 10 wt % FFA. The feedstock can contain about 0 wt % to about 100 wt % glycerides, e.g., from about 10 wt % to about 50 wt % glycerides. The feedstock can contain from about 0 wt % to about 50 wt % cellulosic material (preferable less than about 30 or 40 wt %, but at least about 1, 5, 10, or 15 wt %). The feedstock can contain from about 0 wt % to about 50 wt % protein (preferable less than about 30 wt %, but at least about 1, 5, 10, or 15 wt %). Each of the amounts for the feedstock components listed above is based on the dry weight of the feedstock.

The feedstock can be unextracted meaning that it has not been purified to remove certain components (e.g., water, cellulosic material, proteins, or mixtures thereof). For example, the feedstock can contain phospholipids, FFAs, glycerides, at least about 10 wt % cellulosic material, and at least about 10 wt % proteins, wherein both weight percentages are based on the total dry weight of the feedstock. The feedstock can also be purified (e.g., a soapstock or crude vegetable oil). The feedstock can contain husks, shells, or other materials that are grown by the feedstock source other than the feedstock. Materials that contain both oil and cellulosic components lead to attractive renewable fuel alternatives. The feedstock, prior to reaction, can be dried as, e.g., discussed below. The feedstock can be ground to reduce its particle size prior to reaction.

For purposes of this description, algae, such as cyanobacteria, is used as the feedstock, however those skilled in the art would understand that other feedstock can be used. Also, the overall process is, as indicated, applicable to the other feedstocks with adjustments to the process configuration, e.g. if a dry distillers grain or dry rice bran is used as a feedstock, then the drying step would not be required.

In addition, with other feedstocks, there may be some variations in the acid esterification chemistry such that alternate co-products are formed in the reaction. For example, with a high cellulosic feed (e.g., at least about 1, 5, 10, or 15 wt % but less than about 30, 40, or 50 wt % based on the dry weight of the feedstock) there may be further conversion of that component to derivatized sugar compounds such as methyl or ethyl glucosides. For example, when a solution of glucose in methyl alcohol is saturated with hydrochloric acid a crystallizable compound having the formula $C_6H_{11}O_6CH_3$, is formed.

A similar reaction takes place with all of the alcohols which are capable of dissolving glucose, such as methanol, ethanol, propanol, butanol, and their isomers, and the compounds formed correspond to natural glucosides. The sugar entering into the reaction need not necessarily be glucose, so that a number of such artificial alcohol-derivatized sugars can be prepared. The hydrochloric acid of the reaction to produce derivatized sugars can also be replaced by another acid such as $H_2SO_4$. These derivatized sugars, when boiled with dilute acid, react with water and are decomposed into the sugar and alcohol. In addition, further derivatization at the higher ranges of temperatures and pressures can lead to valuable products from the sugars such as methyl glucosides, ethyl glucosides, 5-(hydroxymethyl)furfural, levulinic acid, formic acid, and esters thereof. The categorization of each feedstock may be necessary to determine the best process splits and optimal end-products.

The alcohol for the invention can be, for example, methanol, ethanol, propanol, butanol, isopropyl alcohol, sec-butanol, t-butanol, benzyl alcohol or combination thereof. From a practical standpoint, and for general fuel and potential downstream chemical considerations, alcohols containing from 1 to 5 carbons would be preferred, however, there may be specific situations and conditions wherein higher alcohols could be used. Testing with a specific alcohol would readily determine the amenability of a particular alcohol. Again, for purposes of this discussion, methanol is used as the alcohol, however those skilled in the art would understand that other alcohols can be used. For example, in a combined system that produces both ethanol and biodiesel, it is potentially attractive to use some of the produced ethanol as the alcohol reactant.

The optional acid catalyst for the invention can be, for example, an inorganic acid (e.g., sulfuric acid, anhydrous hydrochloric acid, anhydrous nitric acid, boron trifluoride, and phosphoric acid), an organic acid (e.g. organic sulfonic acid), a solid phase catalyst (e.g., Envirocat™ EPZG, natural kaolinite clay, $B_2O_3/ZrO_2$, sulfated $SnO_2$, and zeolites), or a combination thereof.

For the purposes of this description, sulfuric acid is used as the acid catalyst, however those skilled in the art would understand that other acid catalysts can be used.

Figure 2:
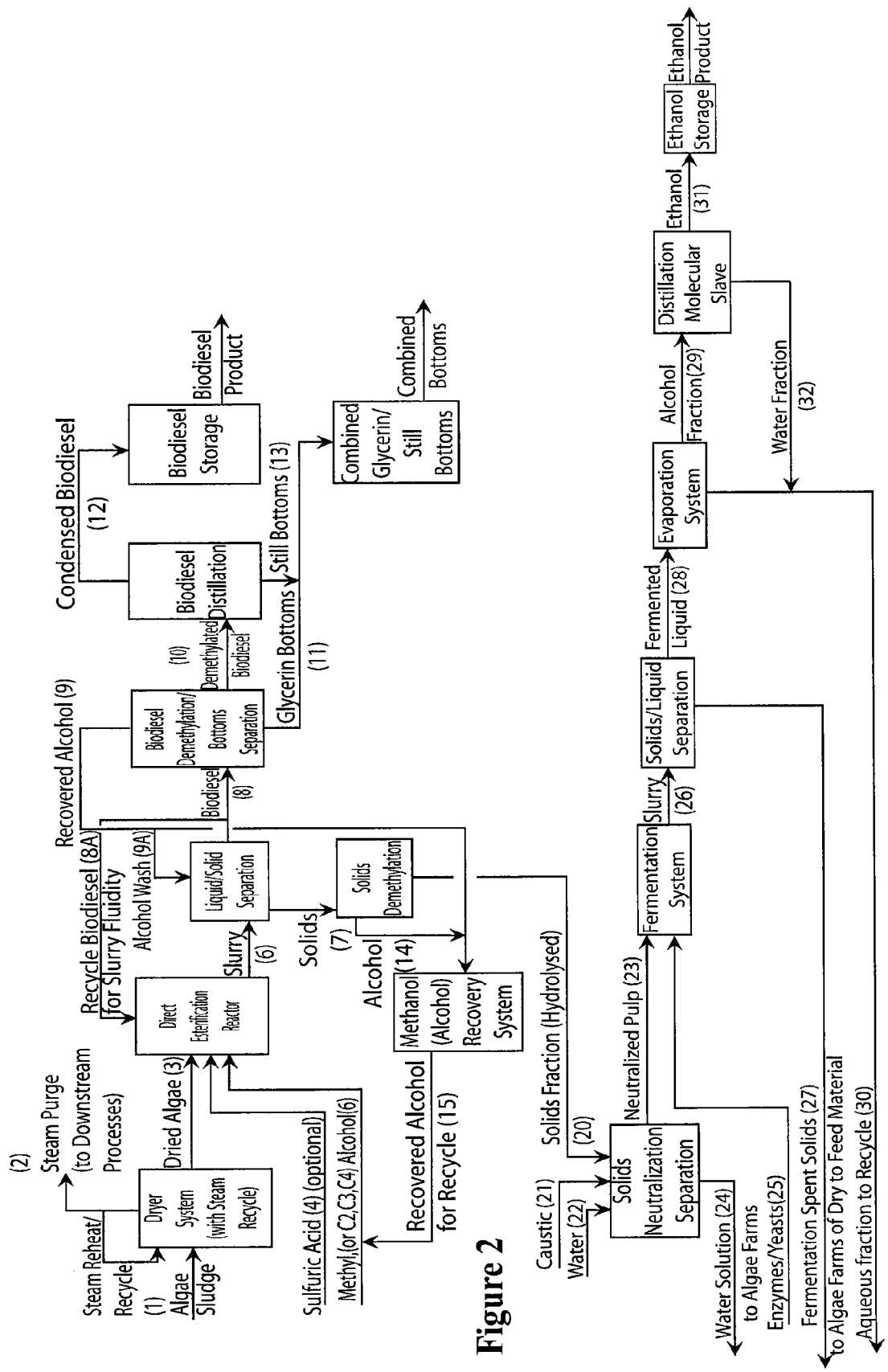
FIG. 2 shows the detailed process concept used for the simultaneous production of biodiesel and ethanol from the algae and/or feedstocks, such as agricultural by-product material. The overall approach is shown for multiple feedstocks. If dry material is received, then the front end drying system would not necessarily be required.

In the process (see FIG. 2), the algae sludge (1), produced via various algae growing processes, e.g. the recovery of $CO_2$ from a power plant or other major $CO_2$ producing stack gases, or other feedstock is first dried in a flash drying system wherein a recycled stream of superheated steam is used to dry the feedstock. The water content of the feedstock after drying can be about 0 wt % to about 10 wt % of the dry weight of the feedstock, from about 3 wt % to about 10 wt % of the dry weight of the feedstock, or from about 3 wt % to about 5 wt % dry weight of the feedstock. The resulting steam, from the wet material, is purged from the system (2) and used for downstream process heat.

Systems that are useful for this step include spin flash dryers; spray dryers; loop dryers; and the like. The main criterion for dryer choice is that the system can be operated at elevated pressure to allow for production of reasonably usable purge steam. A pressure of 10 psig to 30 psig is preferred with 15 psig to 20 psig most preferred. Drying can be carried out at atmospheric pressure, however, in this case the resulting vapor from the dryer cannot be reused for downstream steam uses. Pressurized drying enhances the overall economics of the process, but is not essential for practice of the technique, i.e. atmospheric drying is acceptable, recognizing the economics of the system.

The dried algae (3) or other feedstock can be ground to reduce its particle size and is then transferred to the Direct Esterification Reactor system wherein the feedstock is mixed with the selected alcohol (e.g., methanol) (5), and an optional acid catalyst (4). The amount of alcohol can vary, but would typically be sufficient to allow for a slurry mixture. This typically provides sufficient excess of alcohol for the reaction noting that 3 moles of alcohol are required for reaction with 1 mole of triglycerides to form 3 moles of fatty acid alkyl esters and 1 mole of alcohol is required for reaction with 1 mole of FFAs to form 1 mole of fatty acid alkyl esters. As a minimum, the amount of alcohol should be in about a 15% molar excess of the contained oil. Preferably, the alcohol should be in an amount from about 50 mol % to about 600 mol % of the contained oil (i.e., phospholipids, glycerides, FFAs, or a combination thereof), preferably from about 50 mol % to about 320 mol % of the contained oil and most preferably from about 200 mol % to about 300 mol % of the contained oil. On a weight percentage basis, the contained oil will require about 11% to 12% by weight of methanol to form the methyl ester. Higher alcohols would require a higher weight percentage of alcohol. For practical operation, the amount of alcohol would normally be in the range of about 50 wt % to 300 wt % of the dry feedstock and preferably in the range of about 100 wt % to about 200 wt % of the dry feedstock.

To reduce the amount of alcohol used, and subsequently reduce the downstream demethylation requirements, a portion of the produced biodiesel (8A) can be recycled to the reactor to provide liquid for slurry formation. The amount of fatty acid alkyl ester (i.e., biodiesel) added to the reaction can be in an amount from about 50 wt % to about 300 wt %, preferably from about 100 wt % to about 200 wt %, and most preferably from about 125 wt % to about 150 wt % of the dry weight of the feedstock.

This will allow for introduction of alcohol in amounts sufficient to provide the amount required for the reaction, plus some excess to ensure complete reaction. In this case, the amount of make-up alcohol (e.g. methanol) could be in the range of 5% to 15% by weight of the dry input feedstock.

The amount of optional acid catalyst can range from about 0% to about 15% by weight of the dry feedstock, preferably from about 3% to about 9% by weight of the dry feedstock, and most preferably from about 4% to about 8% by weight of the dry feedstock. The final amount of acid will depend on the composition of the feedstock, since there may be acid consuming compounds in the feed, e.g. reactive protein materials and the like. Thus the actual acid rate will depend on this factor. From a general process consideration standpoint, the key process factor is the amount of "free catalyst" in the system, i.e. free acid after consideration of any components in the feedstock that will consume acid. Preferably the amount of free acid remaining in the mixture is such that the resulting pH of the slurry is in the range of about 0 to about 5, preferably from about 1 to about 4, and most preferably in the range of about 2 to about 3.

In the presence of acid catalyst, the reaction temperature is, e.g. in the range of about 140° C. to about 300° C., in the range of about 160° C. to about 275° C., or in the range of about 175° C. to about 275° C. A pressure reactor system is used that will allow for the elevated temperature and keep the alcohol from boiling in the presence of acid catalyst. The pressure of reactor operation is slightly in excess of the vapor pressure of the alcohol of choice at the selected operating temperature (e.g. 20 psig over the vapor pressure). Typical pressures ranges for a reaction in the presence of acid catalyst are from about 150 psig to about 650 psig, preferably from about 200 psig to about 500 psig, and most preferably from about 300 psig to about 400 psig. Pressures significantly in excess of the alcohol vapor pressure are not required in the process approach.

In the absence or reduction of acid catalyst (e.g., in the range from about 0.01 to 1 wt % based on the dry weight of the feedstock), the temperature of the reaction is increased to a range of about 240° C. to about 300° C., about 240° C. to about 270° C., or about 250° C. to about 280° C. The pressure of the reaction in the absence of acid catalyst is increased to a range of about 500-2800 psig, from about 1000-2000 psig, or from about 1500 to 2000 psig. The initial pH of the reaction in the absence of acid catalyst is in the range of 0 to 7 or in the range of 5 to 7.

When the acid content is eliminated or significantly reduced in the absence of water under the conditions of the above paragraph, a yield towards cellulosic sugar formation, ester formation, and derivatized sugar formation and away from the acid consuming peptide polymer breakdown is observed. In the presence of water as described in below and the absence of acid under the conditions of the above paragraph, ester formation from glycerides, FFAs, and phospholipids, sugar polymer breakdown, and peptide polymer breakdown are observed.

The reaction mixture before reaction can also contain water in an amount of at least about 3 wt % of the dry weight of the feedstock, at least about 5 wt % of the dry weight of the feedstock, at least about 10 wt % of the dry weight of the feedstock, at least about 30 wt % of the dry weight of the feedstock, at least about 40 wt % of the dry weight of the feedstock, or at least about 50 wt % of the dry weight of the feedstock. The reaction mixture before reaction preferably contains water in an amount from about 30 wt % to about 40 wt % of the dry weight of the feedstock.

The reactor system can be batch or continuous. There are several conventional pressure vessel systems available that will operate in batch and continuous modes and the process lends itself to the "conventional" methods for this stage.

In addition, a continuous pipe-type reactor can be used to carry out the reaction. The reactor is a pipe with sufficient residence time to allow for the reaction to complete and is operated under the target pressure and temperature range. The pipe allows for reasonable reaction to occur with minimized vessel complexity.

The reaction can be carried out for a period of about 5 minutes to 120 minutes and the reaction time can depend on the selected reaction system and operating temperature. In a conventional stirred tank reactor, the reaction time can be in the range of 60 to 90 minutes for a batch reactor. At higher temperatures, and corresponding pressures, the reaction time can be reduced.

The reaction product slurry (6) typically consists of the algae pulp (containing cleaved cellulosic material, shortened peptides, and amino acids), crude biodiesel, excess alcohol, catalyst, water and glycerin. The resulting fatty acid alkyl esters will be in the range of 10-50 wt % of the product slurry. The resulting peptides/amino acids will be in the range of 0-50 wt % of the product slurry. The resulting cleaved cellulosic materials will be in the range of 0-50 wt % of the product slurry. The reaction slurry is transferred to a Liquid/Solid Separation system. In this step, the liquid fraction is separated from the solids portion. Separation can be carried out using any number of standard separation techniques, such as filtration, centrifugation, combinations of each approach, and the like. Slight washing of the solids, in the separation device, can be carried out with a small amount of the alcohol (9A) recovered for recycle. The spent wash would then be added into the crude biodiesel fraction.

The washed solids (7) are then sent to a demethylation step wherein the methanol (or other alcohol) is removed from the material via heating. Steam, from the aforementioned drying system can be used for this step. The recovered alcohol (14) is transferred to the Methanol (Alcohol) Recovery System. The solids fraction (20) is transferred, for example, to the ethanol production portion of the process.

The crude biodiesel liquid from the separation (8) is then sent to a Biodiesel Demethylation/Bottoms Separation system. In this process step, the liquid is first demethylated, i.e. alcohol removal, and the vaporized alcohol (9) sent to the Methanol (Alcohol) Recovery System. In the recovery system, the alcohol is distilled to eliminate traces of moisture then returned (15) to the reaction system for reuse.

When the alcohol is removed from the crude biodiesel, the co-products, i.e. water and glycerin separate from the biodiesel fraction. The catalyst reports to the aqueous/glycerin phase. This two phase system is then treated in a separation system, e.g. settling, centrifugation, and the like. The separated water/glycerin/catalyst is referred to as the "bottoms"

fraction. This material (11) is transferred to a storage tank for subsequent disposition. Depending on the feedstock, the bottoms from the demethylation/bottoms separation step may contain high levels of protein-bearing materials. In this case, the protein-rich fraction (11A) can be sent to a separate surge and (if desirable) downstream processes for further separation of the protein fraction from the remainder of the material.

The demethylated biodiesel (10) is then sent to the Biodiesel Distillation unit. In this step, the biodiesel is heated to about 340° F. to 360° F. and subject to a high vacuum in the range of 750 mm to 755 mm Hg (vacuum). Under these conditions, the biodiesel fraction vaporizes and separates from the various lower volatility impurities in the liquid.

The biodiesel vapor is then condensed using conventional indirect heat exchangers with cooling supplied by cooling water. The condensed biodiesel (12) is the transferred to biodiesel storage tanks where the material is analyzed and confirmed for shipment.

The demethylated solids (20) are transferred to a Solids Neutralization/Separation system. In this stage, the pulp is mixed with water (22) and a caustic solution (21), e.g. sodium hydroxide, potassium hydroxide, etc. Ideally potassium hydroxide is used since the resulting potassium salt, i.e. potassium sulfate, is a feed source for the downstream fermentation process. The material is neutralized to a pH of about 5.5 to 7.0. The target pH is that which is consistent with the specific reagent used in the fermentation process.

After neutralization, the slurry can be subjected to a separation step, if required, to remove a portion of the aqueous fraction with an accompanying removal of dissolved salts. This solution (24) would be returned to the algae farms and the potassium sulfate salt used as a food make-up source for the algae material.

The neutralized pulp (23) then enters a Fermentation System wherein it is mixed with conventional fermentation reagents (25), e.g. yeasts, etc., then allowed to react in a conventional fashion. Information relative to the conventional processing approaches are available on numerous websites and a significant resource is the Renewable Fuels Association (available on the WorldWideWeb at rfa.org), which is the key industry trade association. The main advantage is that a potentially lower cost feedstock has now been made available that does not involve a current agricultural food source commodity but rather second generation non food materials such as algae or agricultural by-products.

In the fermentation system, the cellulosic sugars convert to ethanol, with the co-production of carbon dioxide. The $CO_2$ fraction would normally be vented back to the $CO_2$ recovery system for pick-up by the algae used in the carbon dioxide recovery system if algae are used.

The fermentation slurry (26) is then sent to a Solid/Liquid Separation system, and the non-fermented solids removed from the liquid (beer) phase. Again, conventional separation methods may be utilized, such as filters, centrifuges, and the like. The solids fraction (27) can then be used elsewhere e.g. return to the algae farms as a supplemental food source.

The fermented liquid (28) is transferred to an Evaporation System wherein the alcohol phase is evaporated from the liquid, along with some water. The aqueous fraction from the evaporator (30) is returned to the algae farm system.

The alcohol fraction (29) is next treated in a Distillation/Molecular Sieve system. In this process step, the aqueous alcohol is first distilled, to produce a nominal 95% ethanol material, then processed in a molecular sieve unit to remove the remaining water and produce a 99.5%+ethanol product (31). This operation is conventional and widely used in the current ethanol production industry.

The residual solids from the fermentation stage will contain the non-fermentable materials that may also contain significant levels of useful proteins or amino acids. This solids fraction could be combine with other animal feed products or, depending on the exact nature of the material (based on the feedstock), further processed, via drying, to produce a specialized feed product.

Example 1

Algae Testing

The following example illustrates the basic process approach and resulting product potential for algae feedstocks. Table 1 summarizes a series of tests conducted with algae feedstocks (either fresh or salt water algae) using the process described above. The initial pH was at 0.4. The temperature was between 140-180° C. The pressure was between 200 and 500 psig. The reaction time was between 1-2 hours. The starting algae contained anywhere from 10% to 25% lipid content of which the FFA values ranged from 5% to as much as 10%. The resulting recovered biodiesel indicated that the contained oil was essentially completely converted to the methyl ester. The percent conversion of oil to fatty acid methyl ester was greater than 95%.

TABLE 1

|  | Test | | | | | | |
| --- | --- | --- | --- | --- | --- | --- | --- |
|  | 1 | 2 | 3 | 4 | 5 | 6 | 7 |
| Dry algae (grams) | 1,000 | 1,000 | 1,000 | 1,000 | 1,000 | 1,000 | 1,000 |
| Acid catalyst (grams) | 25 | 25 | 25 | 25 | 25 | 25 | 25 |
| MeOH (grains) | 1500 | 1400 | 1300 | 1200 | 1200 | 1200 | 1200 |
| Results | | | | | | | |
| Dry weight pulp | 550 | 544 | 555 | 539 | 553 | 630.5 | 611 |
| Fatty Acid Methyl Ester (FAME) | 222 | 219 | 224 | 217 | 223 | 94 | 98 |
| Starch | 193 | 191 | 195 | 189 | 194 | 225 | 247.5 |

\* material subjected to temperature and pressure reaction conditions
\* reactor product separated in centrifuge, centrate taken to demethylation
\* two phases observed after demethylation, centrifuged to separate ester from starch/protein
\* minor amounts of material lost in handling through laboratory equipment
\* variations from tests 1-5 and tests 6-7 represent various fresh and salt water algae.
\* Process technique is capable of processing all algae tested into FAME and starch A sample of the solid residue material (i.e., pulp), that contained the starch fraction was then mixed with water and neutralized to a pH of about 6.5-7. Standard ethanol processing yeast was added and the material was allowed to ferment for a period of about 5 days. A small laboratory system was used wherein the mixture was contained in a contained flask. A $CO_2$ discharge tube was located on top of the flask and the $CO_2$ was discharged, via a dip leg, into a separate flask containing water. This maintained a "water seal" on the fermentation flask and also allowed for visual observation of $CO_2$ bubbles, which, when they stopped, indicated fermentation completion.

After the $CO_2$ evolution stopped, the resulting fermentation broth was filtered to remove residual solids. The resulting liquid was heated to evaporate a mixture of ethanol and water in a single stage evaporation flask with a condenser. The condensed ethanol water phase contained about 8% ethanol. In commercial practice, the weak ethanol would be treated in a conventional evaporation/distillation/molecular sieve system (e.g. the standard approach used in the conventional ethanol production processes) to recover an anhydrous ethanol product. The techniques are well established, and again reference is made to the Renewable Fuels Association website.

About 50% of the contained starch converts to actual ethanol (the remainder forming $CO_2$). The expected ethanol recovery from the algae feedstocks would be on the order of 10% by weight of the algae. This conversion factor will depend on the potential starch content of the starting algae and can vary between various specifies of material. The recovery factors are for illustration and are no way meant to limit the scope or require a specific recovery.

Example 2

Algae Soapstock Testing

Algae soapstock is a by-product of the conventional algae oil processing route wherein the oil, containing high levels of free fatty acids (FFA), is treated with an alkali solution to neutralize the FFA and produce a "soapstock" that consists of neutralized fatty acids. This material is separated from the aqueous salt solution and typically recovered as a "soapstock" material. A similar product is formed, in large amounts, from soybean oil treatment and is sold, at relatively low cost, for subsequent acidulation and recovery of the fatty acid values, as a free fatty acid, for use in animal feeds or other lower valued applications.

To assess the potential for soapstocks as feeds, a sample of algae soapstock was obtained and processed in a manner similar to that outlined for the algae (Example 1), with the exception that a solids/liquid separation after the esterification stage was not required. Briefly, the soapstock was initially neutralized with sulfuric acid, then methanol and additional sulfuric acid was added to provide excess acid (for catalyst). The mass of soapstock was 100 g. The mass of the initial sulfuric acid was 17 g to acidify the soap. The mass of the methanol was 200 g. The additional mass of the sulfuric acid used for the catalyst was 4 g. The initial pH was below 1. The moisture content in the feedstock was on the order of 10 wt % to 15 wt % of the weight of the feedstock, based on the indicated supplier estimates (as supplied by Advanced Bio Nutrition, Columbia, Md.). The mass was reacted for about 2 hours at about 140° C. under pressure sufficient to avoid methanol evaporation.

The reaction mass was then neutralized with lime (to eliminate any free sulfuric acid) and the material then separated via a centrifuge into an aqueous phase, containing the water, glycerin, and salt fraction, and an organic phase. The organic phase containing essentially the biodiesel fraction was then distilled to recover the ester fraction. The resulting biodiesel was analyzed and met the ASTM standards for this material. In this case there was no sugar or starch-like fraction so ethanol is not a consideration for this feedstock.

Of considerable note with this test is that the esterification was carried out in a relatively high free water environment (i.e. in excess of 10% free water), since the soapstock, as indicated, is a neutralized FFA from the oil feed. This is of significance since for the conventional biodiesel processing approaches, including the two stage processes consisting of acid esterification followed by base transesterification, water must be limited, typically to levels of less than 1% to 2% for acid esterification and less than 0.5% for the transesterification step.

Example 3

Distillers Grain

Corn Feedstock

Distillers grain is a major co-product from the production of ethanol using the conventional corn feedstocks. Dry distillers grain (DDG) is the material remaining after the fermentation process and contains proteins, fats, fiber, ash, and other various components. Much of this material is used in animal feed products, but its value, compared to corn, is lower.

The quantities of this material are significant. For example, a 100 million gallon/year ethanol facility using a dry corn feed would produce on the order of 660 million pound/year of DDG. In general, the DDG from corn contains about 10% to 11% fat (oil content that is potentially convertible to biodiesel) and about 45% to 50% carbohydrates (which if properly prepared could serve as a fermentation feed).

It should be noted that with preparation, the resulting sugars consist of both C6 and C5 fractions. The C6 fraction is fermentable via the use of standard yeast materials. C5 sugars will not ferment with yeasts only, and specialized enzymes have been developed that will convert C5's. In addition, there are other processes that have been developed that utilize C5 sugars to produce other (non-ethanol) products.

Significant advantages could be brought about in the biofuels industries if this feedstock could be further processed to recover additional ethanol and produce a biodiesel product as well. Incorporation of DDG treatment operations within existing ethanol plants could further enhance the potential economic attractiveness.

To assess the potential for the process to handle this feed, samples of DDG from ethanol facilities (Verasun Energy of Brookings, S. Dak. and White Energy of Dallas, Tex.) that processed both corn and sorgum feedstocks were obtained. The basic testing approach was as follows:

The DDG was mixed with methanol and sulfuric acid catalyst then reacted at elevated temperature and pressure for about 2 hours. Typically the temperature was maintained at about 200 deg C. The mass of the DDG was 100 grams, the mass of the methanol was 200 grams, the mass of the sulfuric acid was 8 grams, the initial pH was 0.5.

After reaction, the ester product mass was then filtered and washed with additional alcohol to remove residual ester, sugars, etc.

The solids fraction was then set aside and would be used as a lower grade animal feed in a commercial scenario.

The liquid fraction was then heated to remove excess alcohol (that would be recovered for recycle in a commercial scenario).

The mixture was then neutralized to convert the free sulfuric acid to a neutral salt. Neutralizing agents can include common alkalis, e.g. sodium hydroxide, potassium hydroxide, sodium bicarbonate, potassium carbonate, calcium oxide, calcium hydroxide, etc. The use of calcium is ideal since it allows for subsequent animal feed nutrition. The liquid, containing the esters, glycerine, derivitized sugars, amino acids and the like was treated in an additional separation stage to remove the ester fraction from the non-ester fraction. Several methods are available for this including solvent extraction, with e.g. hexane, or water dissolution (preferred) to solublize the glycerin and sugar fraction and allow for separation of the ester as an separate phase (i.e. liquid/liquid separation).

The ester fraction was then treated in a distillation system to recover the ester as a high grade material.

The sugar, amino acid fraction (non-esters) was then neutralized and, if a calcium material used, filtered to remove the resulting calcium sulfate salt. This has the effect of reducing the potential ash in the final amino acid.

With the reaction conditions employed, derivatized sugars, such as 5-(hydroxymethyl)furfural, were formed which will allow for potential production and recovery of other products.

For the example test the material used was the corn DDG and contained about an 11 wt % oil fraction based on the total weight of the DDG. The above process was carried out and after separation and analysis, the resulting biodiesel fraction was about 10% by weight of the feed, indicating that essentially all of the contained oil was converted to the ester.

The ester fraction was then distilled and the recovered biodiesel analyzed for total and free glycerin, since these are the key components of successful ester production based on previous laboratory testing. The material was well below the allowable ASTM standards.

Example 4

Rice Bran

Rice bran is another material that is a major co-product of this grain processing industry. There are significant amounts of this material produced in the U.S. and especially overseas. The bulk of this material is used in various feed additives and has a relatively low value.

A sample of rice bran was processed in the same manner as that used for the DDG sample (in Example 3). The composition of the bran was somewhat similar to that of the DDG with respect to carbohydrate content (i.e. potentially fermentable) but the oil content was somewhat higher (typically 18 wt % or so).

After ester recovery, the material was distilled and the biodiesel analyzed. Again the material was well within specifications. Also, the amount of biodiesel produced was in line with the expected value based on the oil content. Several tests have indicated that the expected biodiesel production is about the same (volume-wise) as the oil content in the starting feedstock.

The remaining treated carbohydrate fraction would then normally be subject to fermentation since the composition at this stage is similar to the material obtained in the DDG processing.

Example 5

Analysis of Cyanobacteria for Free Neutral Lipid and Free Phospholipid Content

The cyanobacteria sample was stored at −20° C. until analysis. Appropriate weights of the sample were diluted with Hexane:Isopropanol for neutral lipid analysis and Chloroform:Methanol for phospholipid analysis. Samples were vortexed, sonicated, and syringe filtered prior to injection for HPLC analysis to extract the free lipids (i.e., lipids not bound to protein) of the sample.

HPLC Analysis. Neutral lipid analysis was performed by gradient normal phase high performance liquid chromatography with evaporative light scattering detection. For neutral lipid determination, standards consisted of TG, DG, MG, and FFA at 1.0 mg/ml-0.03125 mg/ml each, For phospholipid determination, the standards and the sample were injected on a normal phase HPLC column and analyzed by evaporative light scattering detector. The six-level calibration curve was used to calculate the amount of each phospholipid in the sample. HPLC standards for phospholipids consisted of Soy PC, Soy PE, Soy PI, Soy LPC, Soy PS and 16:0-18:1 PA at 1.0 mg/ml-0.0625 mg/ml each.

Results. Table 2 reports the weight (w/w) percent results of the neutral lipid analysis. Table 3 reports the weight (w/w) percent results of the phospholipid analysis.

TABLE 2

Neutral lipids in weight %.

| Sample | TG | DG | FFA | MG | Total |
|---|---|---|---|---|---|
| Spirulina Lot 9808 | 2.8 | 0.2 | 0.2 | ND | 3.2 |

ND = none detected; TG, triglycerides; DG, diglycerides; FFA, free fatty acids; MG, monoglycerides.

TABLE 3

Phospholipids in weight %.

| Sample | PE | PC | PA | PI | PS | LPC | Total |
|---|---|---|---|---|---|---|---|
| Spirulina Lot 9808 | 1.2 | ND | ND | ND | ND | ND | 1.2 |

ND = none detected; PE, phosphotidylethanolamine; PC, phosphotidylcholine; PA, phosphatidic acid; PI, phosphatidylinositol; PS, phosphatidylserine; LPC, lypophosphotidylcholine.

The total free lipid content was 4.4 wt %. Based on these results, a sample of cyanobacteria was expected to yield 4 wt % fatty acid methyl esters (FAMEs) based on the total weight of cyanobacteria and assuming 100% conversion of the free lipid content to FAMEs.

Example 6

Cyanobacteria Testing using the Discovered Method

The following example illustrates the process and resulting product for cyanobacteria feedstocks. Fifty grams of dry cyanobacteria, 0 grams of [what kind] acid catalyst, 20 grams of water and 100 grams of methanol were reacted. No acid catalyst was added to the reaction. The temperature was between 250 C-280° C. The pressure was between 1500 and 1900 psig. The reaction time was between 5-30 minutes. The starting algae was expected to contain from 4 wt % to 6 wt % lipid content of which the phospholipid values ranged from 1 wt % to 2 wt %.

The resulting reaction products were centrifuged to separate the solid material (i.e., pulp) from the biofuel. The biofuel was demethylated as described above. The pulp from centrifugation can be processed into, for example, ethanol as described above.

The experiment was repeated two times generating 8 grams (16 wt % based on the total weight of the cyanobacteria starting material) and 10 grams (20 wt % based on the total weight of the cyanobacteria starting material) of FAMEs, respectively. Table 4 lists the types and percentage amounts of FAMEs in the 10 gram sample. These results indicated that the contained oil, including the phospholipids, was essentially completely converted to fatty acid methyl esters. In addition, the amount of FAMEs generated was about 4 to 5 more than expected based on the total free lipid content of cyanobacteria as observed in Example 5. The reaction also generated 75-80 wt % of dry pulp and 5 wt % ash.

TABLE 4

| FFA | M.W. | FAME (uM) | FAME (mM) | Dilution 1E3 | FAME (mg/ml) | Percent FAME |
|---|---|---|---|---|---|---|
| UNK | 228.38 | 92.4 | 0.0924 | 1000 | 21.1 | 0.89 |
| UNK | 228.38 | 42.5 | 0.0425 | 1000 | 9.7 | 0.41 |
| 14:0 FFA | 228.38 | 553.2 | 0.5532 | 1000 | 126.3 | 5.31 |
| 15:0 FFA | 242.21 | 54.8 | 0.0548 | 1000 | 13.3 | 0.56 |
| UNK | 242.21 | 30.2 | 0.0302 | 1000 | 7.3 | 0.31 |
| 16:0 FFA | 256.43 | 2385.1 | 2.3851 | 1000 | 611.6 | 25.70 |
| UNK | 256.43 | 101.6 | 0.1016 | 1000 | 26.1 | 1.09 |
| 16:1 FFA | 254.43 | 1966 | 1.966 | 1000 | 500.2 | 21.02 |
| UNK | 254.43 | 172.7 | 0.1727 | 1000 | 43.9 | 1.85 |
| UNK | 254.43 | 62.6 | 0.0626 | 1000 | 15.9 | 0.67 |
| UNK | 254.43 | 36.7 | 0.0367 | 1000 | 9.3 | 0.39 |
| 17:0 FFA | 270.48 | | 0 | 1000 | 0.0 | 0.00 |
| UNK | 270.48 | 64 | 0.064 | 1000 | 17.3 | 0.73 |
| 17:1 FFA | 268.48 | | 0 | 1000 | 0.0 | 0.00 |
| 18:0 FFA | 284.48 | 57.3 | 0.0573 | 1000 | 16.3 | 0.68 |
| 18:1 FFA | 282.48 | 449 | 0.449 | 1000 | 126.8 | 5.33 |
| 18:2 FFA | 280.48 | 280.1 | 0.2801 | 1000 | 78.6 | 3.30 |
| UNK | 280.48 | 49.4 | 0.0494 | 1000 | 13.9 | 0.58 |
| 18:3 FFA | 278.48 | 57.9 | 0.0579 | 1000 | 16.1 | 0.68 |
| 19:0 FFA | 298.51 | | 0 | 1000 | 0.0 | 0.00 |
| 20:0 FFA | 312.54 | | 0 | 1000 | 0.0 | 0.00 |
| 20:1 FFA | 310.54 | | 0 | 1000 | 0.0 | 0.00 |
| 20:2 FFA | 308.53 | | 0 | 1000 | 0.0 | 0.00 |
| UNK | 308.53 | 58.5 | 0.0585 | 1000 | 18.0 | 0.76 |
| 20:4 FFA | 304.52 | 277.2 | 0.2772 | 1000 | 84.4 | 3.55 |
| UNK | 304.52 | 167.9 | 0.1679 | 1000 | 51.1 | 2.15 |
| UNK | 304.52 | 136 | 0.136 | 1000 | 41.4 | 1.74 |
| 20:5 FFA | 302.54 | 790.1 | 0.7901 | 1000 | 239.0 | 10.04 |
| UNK | 302.54 | 250.7 | 0.2507 | 1000 | 75.8 | 3.19 |
| UNK | 302.54 | 151.9 | 0.1519 | 1000 | 46.0 | 1.93 |
| UNK | 302.54 | 600.8 | 0.6008 | 1000 | 181.8 | 7.64 |
| UNK | 302.54 | 64.5 | 0.0645 | 1000 | 19.5 | 0.82 |
| 22:6 FFA | 328.57 | | 0 | 1000 | 0.0 | 0.00 |

The disclosed process has been tested with a variety of oil/starch-containing feedstocks as well as high soap materials. The examples are shown for illustration purposes only and in no way restrict the scope as to the potential feedstocks that are suitable for this approach.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein, including all patents, published patent applications, and published scientific articles, are incorporated by reference in their entireties for all purposes.

We claim:

1. A method for making fatty acid alkyl esters, the method comprising:
   (a) combining an unextracted feedstock with an alcohol, wherein the feedstock comprises phospholipids, at least 10 wt % cellulosic material based on the dry weight of the feedstock, and at least 10 wt % proteins based on the dry weight of the feedstock and the water content of a combination of the feedstock and the alcohol is at least 10 wt % of the dry weight of the feedstock; and
   (b) reacting the combination of the feedstock and the alcohol at a temperature in the range of 240° C. to 300° C., and at a pressure in a range of 1000 psig to 2000 psig to generate fatty acid alkyl esters from the phospholipids and cleave the cellulosic material and the proteins.

2. The method of claim 1, further comprising drying the feedstock prior to combining the feedstock with the alcohol.

3. The method of claim 1, wherein the alcohol is methanol or ethanol.

4. The method of claim 1, wherein the alcohol is in an amount from 50 wt % to 300 wt % of the dry feedstock.

5. The method of claim 1, wherein the water content of the combination before reaction is from 30 wt % to 40 wt % of the dry weight of the feedstock.

6. The method of claim 1, further comprising adding a fatty acid alkyl ester to the combination before reacting.

7. The method of claim 1, further comprising separating the resulting fatty acid alkyl esters from the resulting cleaved cellulosic material.

8. The method of claim 1, wherein the reaction of the feedstock and the alcohol is performed without an acid catalyst.

9. The method of claim 1, wherein the reaction of the feedstock and the alcohol is performed without catalyst.

10. The method of claim 1, wherein the feedstock is algae, dried distillers grain, or rice bran.

11. The method of claim 1, wherein the water content of the combination before reaction is at least about 50 wt % of the dry weight of the feedstock.

12. The method of claim 1, wherein the cellulosic material is polysaccharides, cellulose, hemicellulose, lignocellulose, or a combination thereof.

* * * * *

UNITED STATES PATENT AND TRADEMARK OFFICE
CERTIFICATE OF CORRECTION

| | | |
|---|---|---|
| PATENT NO. | : 7,943,792 B2 | Page 1 of 1 |
| APPLICATION NO. | : 12/243933 | |
| DATED | : May 17, 2011 | |
| INVENTOR(S) | : William W. Berry et al. | |

It is certified that error appears in the above-identified patent and that said Letters Patent is hereby corrected as shown below:

Title Page;
On the Face Page, in field (56), under (Other Publications), in column 2, line 1, delete "Manufactureo" and insert -- Manufacture of --, therefor.

On the Face Page, in field (56), under (Other Publications), in column 2, line 1, delete "natrual" and insert -- natural --, therefor.

On Page 2, in column 2, line 3, under "Other Publications", delete "decompositoin" and insert -- decomposition --, therefor.

On Page 3, in column 2, line 28, under "Other Publications", delete "Self-oganization" and insert -- Self-organization --, therefor.

In column 1, line 61, delete "13;" and insert -- 13: --, therefor.

In column 6, line 24, delete "trifloride," and insert -- trifluoride, --, therefor.

In column 12, line 49, delete "sorgum" and insert -- sorghum --, therefor.

In column 13, line 11, delete "solublize" and insert -- solubilize --, therefor.

In column 13, line 24, delete "test" and insert -- test, --, therefor.

In column 14, line 10, delete "each," and insert -- each. --, therefor.

Signed and Sealed this
Nineteenth Day of July, 2011

David J. Kappos
*Director of the United States Patent and Trademark Office*